US012767628B2

(12) United States Patent
Lyu et al.

(10) Patent No.: US 12,767,628 B2
(45) Date of Patent: Oct. 20, 2026

(54) METHOD FOR PREPARING ACRYLIC ACID

(71) Applicant: LG CHEM, LTD., Seoul (KR)

(72) Inventors: Byeong Gil Lyu, Daejeon (KR); Mi Kyung Kim, Daejeon (KR); Eun Kyo Kim, Daejeon (KR); Hye Bin Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 608 days.

(21) Appl. No.: 18/265,554

(22) PCT Filed: Aug. 1, 2022

(86) PCT No.: PCT/KR2022/011331
§ 371 (c)(1),
(2) Date: Jun. 6, 2023

(87) PCT Pub. No.: WO2023/063549
PCT Pub. Date: Apr. 20, 2023

(65) Prior Publication Data

US 2024/0025834 A1 Jan. 25, 2024

(30) Foreign Application Priority Data

Oct. 15, 2021 (KR) ........................ 10-2021-0137931
Jul. 25, 2022 (KR) ........................ 10-2022-0091840

(51) Int. Cl.
*C07C 51/377* (2006.01)
*C07C 51/42* (2006.01)

(52) U.S. Cl.
CPC ............ *C07C 51/377* (2013.01); *C07C 51/42* (2013.01)

(58) Field of Classification Search
CPC ....... C07C 45/82; C07C 49/17; C07C 51/377; C07C 51/42; C07C 51/44; C07C 51/48; C07C 57/04
See application file for complete search history.

(56) References Cited

U.S. PATENT DOCUMENTS

| | | | | |
|---|---|---|---|---|
| 2006/0025629 | A1 | 2/2006 | Kang et al. | |
| 2011/0034603 | A1 | 2/2011 | Fujino et al. | |
| 2013/0317253 | A1 | 11/2013 | Baek et al. | |
| 2014/0105792 | A1 * | 4/2014 | Baek | C07C 51/44 422/187 |
| 2015/0105584 | A1 | 4/2015 | Velasquez et al. | |
| 2016/0122272 | A1 | 5/2016 | Lee et al. | |
| 2017/0283358 | A1 | 10/2017 | Jain et al. | |
| 2018/0126187 | A1 | 5/2018 | Collias et al. | |
| 2019/0071382 | A1 | 3/2019 | Fauconet et al. | |

FOREIGN PATENT DOCUMENTS

| | | | |
|---|---|---|---|
| CN | 101255109 | * | 9/2008 |
| CN | 101255109 | A | 9/2008 |
| EP | 3404015 | A1 | 11/2018 |
| JP | 2009-242285 | | 10/2009 |
| JP | 2009-263347 | | 11/2009 |
| JP | 5130107 | | 1/2013 |
| JP | 2014-189510 | | 10/2014 |
| JP | 2016-169162 | | 9/2016 |
| JP | 2016-175840 | | 10/2016 |
| JP | 2016-538113 | | 12/2016 |
| JP | 2020-500180 | | 1/2020 |
| KR | 10-2006-0048785 | | 5/2006 |
| KR | 10-2013-0128847 | | 11/2013 |
| KR | 10-2015-0006349 | | 1/2015 |
| KR | 10-2015-0011634 | | 2/2015 |
| KR | 10-1535496 | | 7/2015 |
| KR | 10-2017-0113177 | | 10/2017 |
| KR | 10-2018-0064432 | | 6/2018 |
| KR | 10-2018-0074314 | | 7/2018 |
| WO | 2009-130915 | | 10/2009 |

* cited by examiner

*Primary Examiner* — Pancham Bakshi
(74) *Attorney, Agent, or Firm* — Bryan Cave Leighton Paisner LLP

(57) ABSTRACT

Provided is a method for preparing an acrylic acid, in which a lactic acid aqueous solution is dehydrated to prepare a reaction product stream, from which by-products are removed using an extraction column, an extractant recovery column, a first separation column, a second separation column, and a refining column to prepare a high-purity acrylic acid.

10 Claims, 2 Drawing Sheets

【FIG. 1】
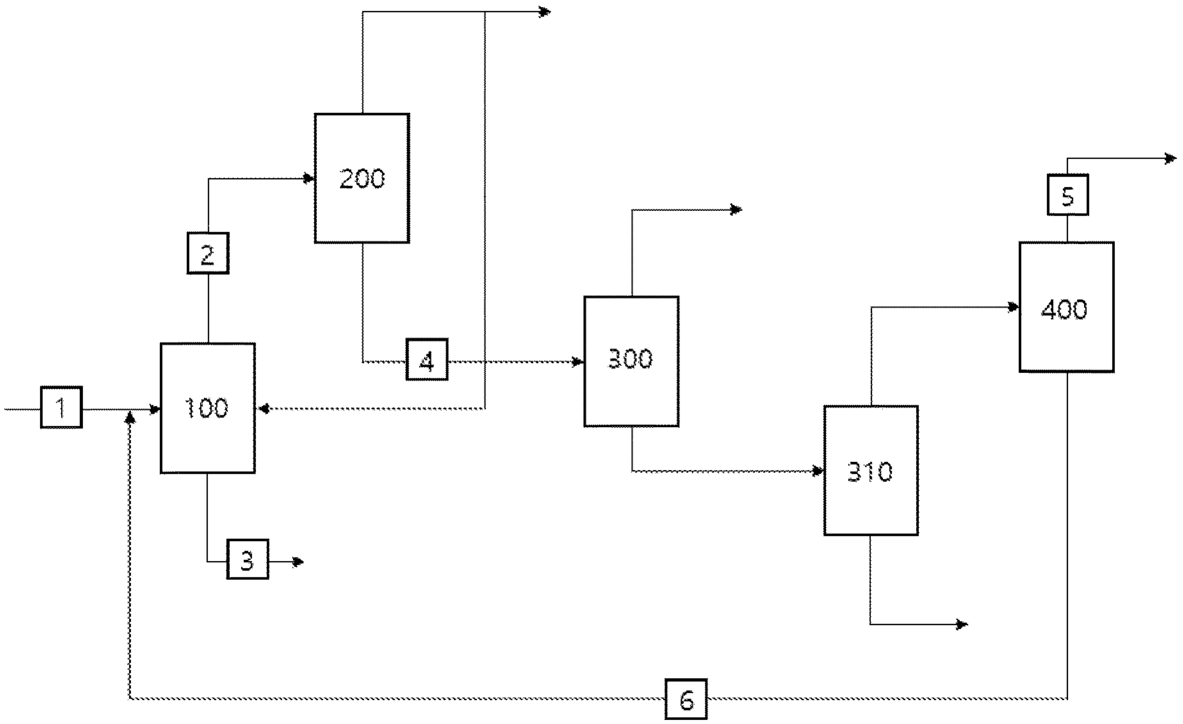
【FIG. 2】
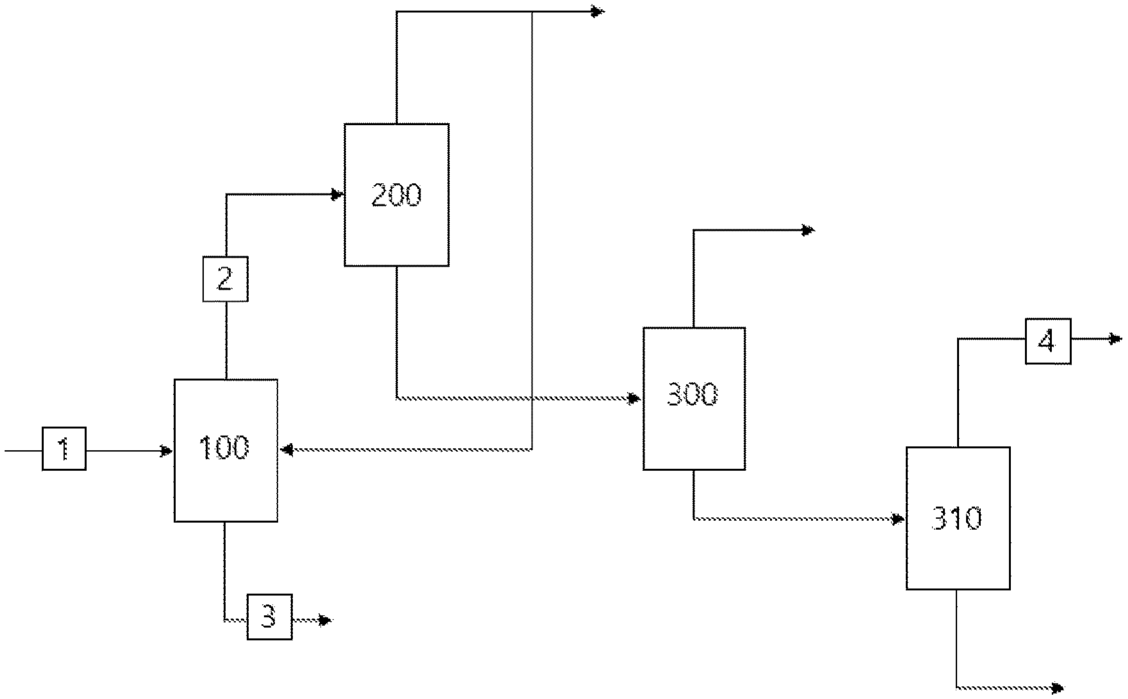

【FIG. 3】
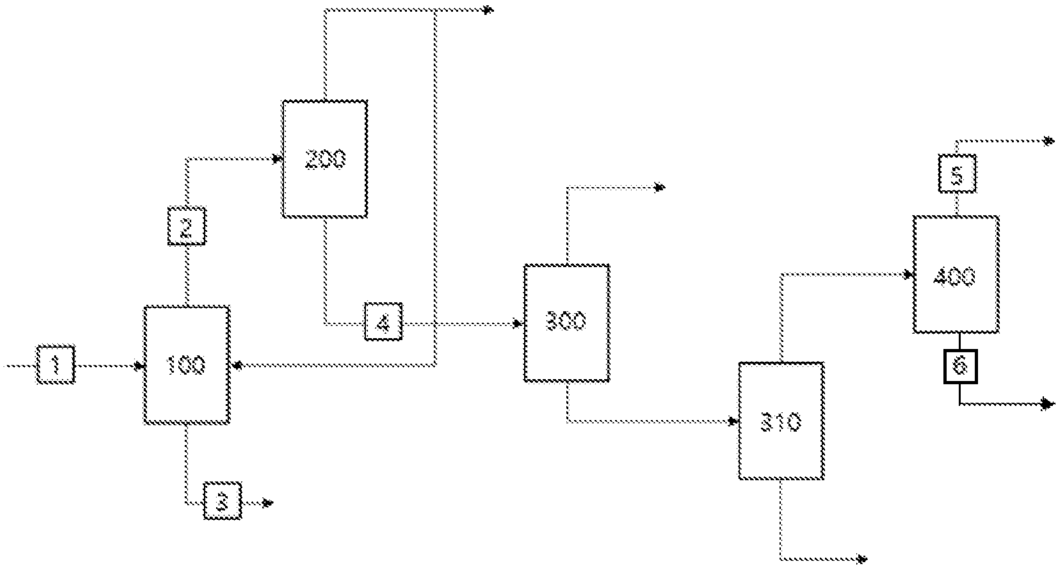

METHOD FOR PREPARING ACRYLIC ACID

CROSS-REFERENCE TO RELATED APPLICATIONS

This application is a National Stage Application of International Application No. PCT/KR2022/011331 filed on Aug. 1, 2022, which claims the benefit of priorities to Korean Patent Application No. 10-2021-0137931, filed on Oct. 15, 2021, and Korean Patent Application No. 10-2022-0091840, filed on Jul. 25, 2022, the entire contents of which are incorporated herein as a part of the specification.

TECHNICAL FIELD

The present invention relates to a method for preparing an acrylic acid, and more particularly, to a method for preparing an acrylic acid by a dehydration reaction of a lactic acid, which effectively removes by-products while reducing an acrylic acid loss.

BACKGROUND

An acrylic acid is used as a polymer raw material used in fiber, adhesives, paint, fiber processing, leather, building materials, and the like, and its demand is growing. In addition, the acrylic acid is also used as a raw material of an absorbent resin and is industrially used a lot in absorbent articles such as paper diapers and sanitary napkins, agricultural and horticultural water retaining agents, industrial water stop materials, and the like.

A conventional method for preparing an acrylic acid is generally a method of oxidizing propylene in the air, but the method is a method of converting propylene into acrolein by a gaseous contact oxidation reaction and subjecting the acrolein to a gaseous contact oxidation reaction to prepare an acrylic acid, and the method produces an acetic acid as a by-product, which is difficult to separate from the acrylic acid. In addition, the method for preparing an acrylic acid using propylene uses propylene obtained by refining crude oil which is a fossil resource, as a raw material, and considering problems such as a recent rise in crude oil prices or global warming, the method has a problem in terms of raw material costs or environmental pollution.

In this regard, a study on a method for preparing an acrylic acid from a carbon-neutral biomass raw material was conducted. For example, there is a method for preparing an acrylic acid (AA) by a gaseous dehydration reaction of a lactic acid (LA). This method is generally a method for preparing an acrylic acid by an intramolecular dehydration reaction of a lactic acid in the presence of a catalyst at a high temperature of 300° C. or higher. However, in the dehydration reaction of the lactic acid, a side reaction occurs in addition to the dehydration reaction, and thus, by-products including hydroxyacetone (HA) are produced in addition to the acrylic acid as a reaction product. In this case, there was a difficult problem in completely removing the hydroxyacetone which is a by-product produced by the dehydration reaction of the lactic acid.

BRIEF DESCRIPTION

Technical Problem

An object of the present invention is to provide a method of minimizing an acrylic acid loss while effectively removing by-products, in preparing an acrylic acid by a dehydration reaction of a lactic acid, in order to solve the problems mentioned in the Background Art.

Technical Solution

In one general aspect, a method for preparing an acrylic acid includes: supplying a reaction product stream prepared by a dehydration reaction of a lactic acid aqueous solution to an extraction column, and in the extraction column, separating an upper discharge stream including an acrylic acid using an extractant and supplying the upper discharge stream to an extractant recovery column; in the extractant recovery column, separating a lower discharge stream including the acrylic acid and supplying the lower discharge stream to a first separation column; in the first separation column, separating a low-boiling point by-product to an upper portion, and separating a lower discharge stream including the acrylic acid and supplying the lower discharge stream to a second separation column; in the second separation column, separating a high-boiling point by-product to a lower portion, and supplying an upper discharge stream including the acrylic acid to a refining column; and in the refining column, separating an upper discharge stream including the acrylic acid, and refluxing a lower discharge stream including hydroxyacetone to the extraction column.

Advantageous Effects

According to the method for preparing an acrylic acid of the present invention, hydroxyacetone having a boiling point similar to the acrylic acid is completely removed from a reaction product including the acrylic acid, thereby solving a problem of the lowered purity of an acrylic acid product due to the residual hydroxyacetone, and minimizing an acrylic acid loss in the process of separating and removing the hydroxyacetone.

DESCRIPTION OF THE DRAWINGS

FIG. 1 is a process flow diagram of a method for preparing an acrylic acid according to an exemplary embodiment of the present invention.

FIGS. 2 and 3 are process flow diagrams of the methods of preparing an acrylic acid according to the comparative examples.

DETAILED DESCRIPTION

The terms and words used in the description and claims of the present invention are not to be construed limitedly as having general or dictionary meanings but are to be construed as having meanings and concepts meeting the technical ideas of the present invention, based on a principle that the inventors are able to appropriately define the concepts of terms in order to describe their own inventions in the best mode.

The term "stream" in the present invention can refer to a fluid flow in a process, or can refer to a fluid itself flowing in a pipe. Specifically, the stream can refer to both a fluid itself flowing in a pipe connecting each device and a fluid flow. In addition, the fluid can include any one or more components of gas, liquid, and solid.

Hereinafter, the present invention will be described in more detail for better understanding of the present invention, with reference to FIG. 1.

According to the present invention, a method for preparing an acrylic acid is provided. More specifically, the method can include: supplying a reaction product stream 1 prepared by a dehydration reaction of a lactic acid aqueous solution to an extraction column 100, and in the extraction column 100, separating an upper discharge stream 2 including an acrylic acid using an extractant and supplying the upper discharge stream 2 to an extractant recovery column 200; in the extractant recovery column 200, separating a lower discharge stream 4 including the acrylic acid and supplying the lower discharge stream to a first separation column 300; in the first separation column 300, separating a low-boiling point by-product to an upper portion, and separating a lower discharge stream including the acrylic acid and supplying the lower discharge stream to a second separation column 310; in the second separation column 310, separating a high-boiling point by-product to a lower portion, and supplying an upper discharge stream including the acrylic acid to a refining column 400; and in the refining column 400, separating an upper discharge stream 5 including the acrylic acid, and refluxing a lower discharge stream 6 including hydroxyacetone to the extraction column 100.

Specifically, a conventional method for preparing an acrylic acid is generally a method of oxidizing propylene in the air, but the method, which is a method of converting propylene into acrolein by a gaseous contact oxidation reaction and subjecting the acrolein to a gaseous contact oxidation reaction to prepare an acrylic acid, produces an acetic acid as a by-product, which is difficult to separate from the acrylic acid. In addition, the method for preparing an acrylic acid using propylene uses propylene obtained by refining crude oil which is a fossil resource, as a raw material, and considering problems such as a recent rise in crude oil prices or global warming, the method has a problem in terms of raw material costs or environmental pollution.

In order to solve the problems of the conventional method for preparing an acrylic acid, a study on a method for preparing an acrylic acid from a carbon-neutral biomass raw material was conducted. For example, there is a method for preparing an acrylic acid (AA) by a gaseous dehydration reaction of a lactic acid (LA). This method is generally a method for preparing an acrylic acid by an intramolecular dehydration reaction of a lactic acid in the presence of a catalyst at a high temperature. However, in the dehydration reaction of the lactic acid, a side reaction occurs in addition to the dehydration reaction, resulting in production of a by-product as a reaction product in addition to the acrylic acid, in particular, production of hydroxyacetone (HA) having a boiling point similar to the acrylic acid. In this case, it was difficult to completely remove the hydroxyacetone by a distillation method.

In this regard, in the present invention, in order to solve the conventional problem, an acrylic acid is prepared by the dehydration reaction of a lactic acid, in which an extraction method is used for completely removing by-products produced therefrom, in particular, hydroxyacetone (boiling point: 145° C.) which has a boiling point similar to the acrylic acid (boiling point: 141° C.) and thus, is difficult to separate, and it is intended to provide a method of completely removing the hydroxyacetone while also minimizing an acrylic acid loss.

According to an exemplary embodiment of the present invention, a reaction product stream prepared by a dehydration reaction of a lactic acid aqueous solution can be supplied to an extraction column 100. Here, the reaction product can be a condensate condensed through a cooling tower.

Specifically, a lactic acid aqueous solution can be supplied to a reactor and dehydrated to prepare a reaction product including an acrylic acid. Here, the dehydration reaction can be performed as a gas phase reaction in the presence of a catalyst. For example, the concentration of the lactic acid in the lactic acid aqueous solution can be 10 wt % or more, 20 wt % or more, or 30 wt % or more and 40 wt % or less, 50 wt % or less, 60 wt % or less, or 70 wt % or less.

The reactor can be a reactor capable of a common dehydration reaction of a lactic acid, the reactor can include a reaction tube filled with a catalyst, and while a reaction gas including volatile components of a lactic acid aqueous solution as a raw material is passed through the reaction tube, a lactic acid can be dehydrated by a gaseous contact reaction to produce an acrylic acid. The reaction gas can further include any one or more dilution gases of water vapor, nitrogen gas, and air for adjusting a concentration, in addition to the lactic acid.

Operation conditions of the reactor can be common dehydration reaction conditions of a lactic acid. Here, the operation temperature of the reactor can refer to a set temperature of a heating medium or the like used for controlling the temperature of the reactor.

A catalyst used in the dehydration reaction of the lactic acid can include, for example, one or more selected from the group consisting of sulfate-based catalysts, phosphate-based catalysts, and nitrate-based catalysts. As a specific example, the sulfate can include $Na_2SO_4$, $K_2SO_4$, $CaSO_4$, and Ale $(SO_4)_3$, the phosphate can include $Na_3PO_4$, $Na_2HPO_4$, $NaH_2PO_4$, $K_3PO_4$, $K_2HPO_4$, $KH_2PO_4$, $CaHPO_4$, $Ca_3(PO_4)_2$, $AlPO_4$, $CaH_2P_2O_7$, and $Ca_2P_2O_7$, and the nitrate can include $NaNO_3$, $KNO_3$, and $Ca(NO_3)_2$. In addition, the catalyst can be supported on a support. The support can include one or more selected from the group consisting of, for example, diatomaceous earth, alumina, silica, titanium dioxide, carbides, and zeolite.

The reaction product prepared by the dehydration reaction of the lactic acid can further include water ($H_2O$) and by-products such as hydroxyacetone, in addition to the acrylic acid which is a desired product.

The reaction product can be supplied to a cooling tower and cooled therein. Specifically, the reaction product prepared by the dehydration reaction of the lactic acid is a gas phase and can be condensed through the cooling tower. Gaseous by-products can be separated from the upper portion of the cooling tower and a liquid condensate can be discharged to the lower portion, and here, the condensate can be a reaction product stream supplied to the extraction column 100 in the present invention.

According to an exemplary embodiment of the present invention, in the extraction column 100, a separate extractant is used to separate the acrylic acid included in the reaction product stream as an upper discharge stream.

The extractant can include, for example, one or more selected from the group consisting of benzene, toluene, xylene, n-heptane, cycloheptane, cycloheptene, 1-heptene, ethylbenzene, methylcyclohexane, n-butylacetate, isobutylacetate, isobutylacrylate, n-propylacetate, isopropylacetate, methylisobutylketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropylbutylether. As a specific example, the extractant can be toluene.

A method of supplying the extractant and performing extraction in the extraction column 100 can be any known method, and for example, any method such as cross current, counter current, and co-current can be used without particular limitation.

In the extraction column 100, the reaction product stream and the extractant can be brought into contact to separate an extract and an extraction residue solution. For example, the extract can be an acrylic acid dissolved in the extractant, and the extract can be discharged as an upper discharge stream from the extraction column 100. Here, the upper discharge stream from the extraction column 100 can be supplied to an extractant recovery column 200.

In addition, the extraction residue solution is wastewater including water and can be separated to the lower portion of the extraction column 100. Here, to the lower portion of the extraction column 100, hydroxyacetone among the by-products can be separated together with water and discharged, but is not all discharged, and partially flows out as an extract and transferred to the rear end with the acrylic acid. Specifically, the amount of extractant used can be adjusted for removing hydroxyacetone in the extraction column 100, but it is difficult to remove the total amount of hydroxyacetone even with the increased amount of the extractant used, and in this case, the content of the acrylic acid discharged with water to the lower portion of the extraction column 100 is increased, which can cause a problem of increasing an acrylic acid loss.

In this regard, in the present invention, the operating conditions of the refining column 400 at the rear end are adjusted to effectively separate hydroxyacetone and reflux it to the extraction column 100, thereby separating and removing a total amount of hydroxyacetone as the lower discharge stream of the extraction column 100, and minimizing an acrylic acid loss at this time.

For example, a ratio of the content of hydroxyacetone separated to the lower portion of the extraction column 100 to the content of hydroxyacetone included in the reaction product stream can be 0.95 to 1, 0.97 to 1, or 0.99 to 1, and specifically, the total amount of hydroxyacetone included in the reaction product stream supplied to the extraction column 100 can be removed in the extraction column 100. Thus, a high-purity acrylic acid can be separated in the refining column 400.

The upper discharge stream 2 from the extraction column 100 can include the acrylic acid, and also, it can include an extractant and hydroxyacetone. The content of hydroxyacetone in the upper discharge stream of the extraction column 100 can be 0.2 wt % to 15 wt %, 3 wt % to 13 wt %, or 5 wt % to 10 wt % of the hydroxyacetone included in the reaction product stream. Specifically, the content of hydroxyacetone in the upper discharge stream of the extraction column 100 is controlled as described above, thereby minimizing the content of the acrylic acid which is lost with water to the lower portion of the extraction column 100, and reducing the amount of energy used for separation in the refining column 400.

According to an exemplary embodiment of the present invention, the upper discharge stream 2 from the extraction column 100 is supplied to the extractant recovery column 200, and in the extractant recovery column 200, a lower discharge stream 4 including the acrylic acid can be separated and supplied to a first separation column 300. In addition, in the extractant recovery column 200, the extractant can be separated as an upper discharge stream, and a part of the upper discharge stream from the extractant recovery column 200 can be refluxed to the extraction column 100 to reuse the extractant. Here, a lower discharge stream from the extractant recovery column 200 can include a low-boiling point by-product, a high-boiling point by-product, and hydroxyacetone as by-products, with the acrylic acid.

The operating conditions of the extractant recovery column 200 vary with the component contents, the kind of extractant, and the like supplied to the extractant recovery column 200. The operating temperature of the extractant recovery column 200 can be, for example, 40° C. to 150° C., 45° C. to 130° C., or 50° C. to 110° C. In addition, the operating pressure of the extractant recovery column 200 can be 35 torr to 300 torr, 70 torr to 250 torr, or 100 torr to 200 torr. When the extractant recovery column 200 is operated as described above, a by-product occurring at a high temperature can be suppressed to increase the recovery rate of the acrylic acid.

According to an exemplary embodiment of the present invention, the first separation column 300 can be for separating a low-boiling point by-product among the by-products included in the reaction product. Specifically, a lower discharge stream 4 from the extractant recovery column 200 can be supplied to a first separation column 300, a low-boiling point by-product can be separated to the upper portion in the first separation column 300, and a lower discharge stream including the acrylic acid can be separated and supplied to a second separation column 310.

According to an exemplary embodiment of the present invention, the second separation column 310 can be for separating a high-boiling point by-product among the by-products included in the reaction product. Specifically, a lower discharge stream from the first separation column 300 can be supplied to the second separation column 310, a high-boiling point by-product can be separated to the lower portion in the second separation column 310, and an upper discharge stream including the acrylic acid can be separated and supplied to a refining column 400.

According to an exemplary embodiment of the present invention, the first separation column 300 and the second separation column 310 can be devices for separation using a boiling point difference between components by distillation, respectively. Here, the low-boiling point by-product and the high-boiling point by-product included in the lower discharge stream from the extractant recovery column 200 are removed as they go through the first separation column 300 and the second separation column 310, or hydroxyacetone having a boiling point similar to the acrylic acid is not separated and discharged together when the acrylic acid is separated as the upper discharge stream from the second separation column 310. Therefore, when the acrylic acid is commercialized with the upper discharge stream from the second separation column 310, the purity of the product is lowered.

In this regard, in the present invention, the upper discharge stream from the second separation column 310 is supplied to the refining column 400, the upper discharge stream 5 including a high-purity acrylic acid and the lower discharge stream 6 including hydroxyacetone and an acrylic acid are separated in the refining column 400, and the lower discharge stream 6 from the refining column 400 is refluxed to the extraction column 100, thereby removing the total amount of hydroxyacetone in the extraction column 100 and separating the acrylic acid in a high purity as the upper discharge stream from the refining column 400.

Specifically, hydroxyacetone in the by-products can be separated together with water to the lower portion of the extraction column 100, but when the total amount of hydroxyacetone is not discharged, not-discharged hydroxyacetone flows out as an extract and is transferred to the rear end with the acrylic acid. In this case, since hydroxyacetone should be separated in the refining column 400, the yield of a high-purity acrylic acid can be lowered.

Meanwhile, the amount of extractant used can be adjusted for removing hydroxyacetone in the extraction column 100, but in this case, it is difficult to remove the total amount of hydroxyacetone even with the increased amount of the extractant used, and in particular, the content of the acrylic acid discharged with water to the lower portion of the extraction column 100 is increased, which can cause a problem of increasing an acrylic acid loss.

Therefore, when the lower discharge stream from the refining column 400 including hydroxyacetone is refluxed to the extraction column 100, thereby separating hydroxyacetone as an extraction residue solution by extraction in the extraction column 100, a total amount of hydroxyacetone introduced into the acrylic acid refinement system can be removed, and also, a high-purity acrylic acid can be obtained in a high yield from the upper portion of the refining column 400.

According to an exemplary embodiment of the present invention, the operating temperature of the refining column 400 can be, for example, 60° C. to 200° C., 80° C. to 150° C., or 90° C. to 110° C. In addition, the operating pressure of the refining column 400 can be 35 torr to 500 torr, 70 torr to 350 torr, or 100 torr to 200 torr. When the refining column 400 is operated as described above, a high-purity acrylic acid is separated as the upper discharge stream without a problem of an acrylic acid loss due to a side reaction, and hydroxyacetone can be separated together as a part of the acrylic acid is discharged as the lower discharge stream.

The upper discharge stream from the second separation column 310 can be supplied to a stage at 50% to 90%, 55% to 85%, or 60% to 80% of the entire number of stages of the refining column 400. By adjusting the supply stage of the refining column 400 to the above range, the separation efficiency of the refining column 400 can be increased, and thus, the composition of the lower discharge stream from the refining column 400 refluxed to the extraction column 100 can be controlled. At this time, the total number of stages of the refining column 400 can be 15 to 70, 18 to 55, or 20 to 35.

The lower discharge stream 6 from the refining column 400 can form a mixed stream with the reaction product stream and be supplied to the extraction column 100. Since the reaction product stream forms a mixed stream with the lower discharge stream from the refining column 400 refluxed in the refining column 400 and supplies to the extraction column 100, the total amount of hydroxyacetone can be removed to the lower portion of the extraction column 100 while minimizing an acrylic acid loss.

According to an exemplary embodiment of the present invention, in the method for preparing an acrylic acid, if necessary, devices such as a distillation column, a condenser, a reboiler, a valve, a pump, a separator, and a mixer can be further installed.

Hereinabove, the method for preparing an acrylic acid according to the present invention has been described and illustrated in the drawings, but the description and the illustration in the drawings are the description and the illustration of only core constitutions for understanding of the present invention, and in addition to the process and devices described above and illustrated in the drawings, the process and the devices which are not described and illustrated separately can be appropriately applied and used for carrying out the method for preparing an acrylic acid according to the present invention.

Hereinafter, the present invention will be described in more detail by the examples. However, the following examples are provided for illustrating the present invention, and it is apparent to a person skilled in the art that various modifications and alterations can be made without departing from the scope and spirit of the present invention and the scope of the present invention is not limited thereto.

EXAMPLES

Example 1

According to the process flow diagram illustrated in FIG. 1, a process of preparing an acrylic acid was simulated, using an Aspen Plus simulator from Aspen Technology, Inc.

Specifically, a lactic acid aqueous solution having a concentration of 50 wt % and nitrogen ($N_2$) as dilution gas were supplied to a reactor to produce a reaction product including an acrylic acid (AA) by a dehydration reaction, a reactor discharge stream including the reaction product was supplied to a cooling tower, and in the cooling tower, a gaseous by-product was separated to the upper portion, and a liquid reaction product as a condensate 1 was supplied to an extraction column 100.

In the extraction column 100, toluene was used as an extractant to separate an acrylic acid as an upper discharge stream 2, which was supplied to an extractant recovery column 200, and water 3 was separated to the lower portion. At this time, the operating temperature of the extraction column 100 was controlled to 40° C., and the operating pressure was controlled to 750 torr.

In the extractant recovery column 200, the extractant was separated as the upper discharge stream, and a part of the upper discharge stream from the extractant recovery column 200 was refluxed to the extraction column 100. In addition, the lower discharge stream 4 from the extractant recovery column 200 including the acrylic acid was supplied to the first separation column 300. At this time, the operating temperature of the extractant recovery column 200 was controlled to 54.1° C. in the upper portion and 96.9° C. in the lower portion, and the operating pressure thereof was controlled to 110 torr.

In the first separation column 300, a low-boiling point by-product was separated to the upper portion, and the lower discharge stream including the acrylic acid was supplied to a second separation column 310. In addition, in the second separation column 310, a high-boiling point by-product was separated to the lower portion, and the upper discharge stream including the acrylic acid was supplied to the 15th stage of a refining column 400.

In the refining column 400, a high-purity acrylic acid 5 was separated to the upper portion, and the lower discharge stream 6 including hydroxyacetone as a by-product and an acrylic acid was refluxed to the extraction column 100. At this time, the operating temperature of the refining column 400 was controlled to 62.5° C. in the upper portion and 65.6° C. in the lower portion, the operating pressure was controlled to 110 torr, and the total number of stages of the refining column 400 was 20.

At this time, the temperature, the pressure, and the flow rate (kg/hr) for each component in each stream are shown in the following Table 1:

TABLE 1

| | | 1 | 2 | 3 | 4 | 5 | 6 |
|---|---|---|---|---|---|---|---|
| Temperature (° C.) | | 40.0 | 40.0 | 40.0 | 96.9 | 62.5 | 65.6 |
| Pressure (torr) | | 750 | 750 | 750 | 110 | 110 | 110 |
| Mass flow rate (kg/hr) | | 923.4 | 3325.3 | 612.0 | 305.5 | 300.0 | 5.6 |
| Water | | 600.0 | 13.9 | 588.1 | 0.0 | 0.0 | 0.0 |
| Toluene | | 0.0 | 2999.0 | 0.5 | 0.0 | 0.0 | 0.0 |
| Acrylic acid | | 303.4 | 310.9 | 3.4 | 304.0 | 300.0 | 4.1 |
| Hydroxyacetone | | 20.0 | 1.5 | 20.0 | 1.5 | 0.0 | 1.5 |
| Mass fraction | Water | 0.650 | 0.004 | 0.961 | 0.000 | 0.000 | 0.000 |
| | Toluene | 0.000 | 0.902 | 0.001 | 0.000 | 0.000 | 0.000 |
| | Acrylic acid | 0.329 | 0.093 | 0.006 | 0.995 | 1.000 | 0.732 |
| | Hydroxyacetone | 0.022 | 0.000 | 0.033 | 0.005 | 0.000 | 0.268 |
| | Total | 1 | 1 | 1 | 1 | 1 | 1 |

Example 2

The process was performed in the same manner as in Example 1, except that the concentration of the lactic acid aqueous solution was 20 wt %.

At this time, the temperature, the pressure, and the flow rate (kg/hr) for each component in each stream are shown in the following Table 2:

TABLE 2

| | | 1 | 2 | 3 | 4 | 5 | 6 |
|---|---|---|---|---|---|---|---|
| Temperature (° C.) | | 40.0 | 40.0 | 40.0 | 97.0 | 62.5 | 65.6 |
| Pressure (torr) | | 750 | 750 | 750 | 110 | 150 | 150 |
| Mass flow rate (kg/hr) | | 627.2 | 2108.8 | 524.3 | 101.5 | 100 | 1.5 |
| Water | | 500.0 | 4.6 | 496.7 | 0.0 | 0.0 | 0.0 |
| Toluene | | 0.0 | 1999.5 | 0.5 | 0.0 | 0.0 | 0.0 |
| Acrylic acid | | 102.3 | 103.8 | 2.3 | 100.7 | 100.0 | 0.7 |
| Hydroxyacetone | | 25.0 | 0.8 | 25.0 | 0.8 | 0.0 | 0.8 |
| Mass fraction | Water | 0.797 | 0.002 | 0.947 | 0.000 | 0.000 | 0.000 |
| | Toluene | 0.000 | 0.948 | 0.001 | 0.000 | 0.000 | 0.000 |
| | Acrylic acid | 0.163 | 0.049 | 0.004 | 0.992 | 1.000 | 0.467 |
| | Hydroxyacetone | 0.040 | 0.000 | 0.048 | 0.008 | 0.000 | 0.533 |
| | Total | 1 | 1 | 1 | 1 | 1 | 1 |

COMPARATIVE EXAMPLES

Comparative Example 1

According to the process flow diagram illustrated in FIG. 2, a process of preparing an acrylic acid was simulated, using an Aspen Plus simulator from Aspen Technology, Inc.

Specifically, a lactic acid aqueous solution having a concentration of 50 wt % and nitrogen ($N_2$) as dilution gas were supplied to a reactor to produce a reaction product including an acrylic acid (AA) by a dehydration reaction, a reactor discharge stream including the reaction product was supplied to a cooling tower, and in the cooling tower, a gaseous by-product was separated to the upper portion, and a liquid reaction product as a condensate 1 was supplied to an extraction column 100.

In the extraction column 100, toluene was used as an extractant to separate an acrylic acid as an upper discharge stream 2, which was supplied to an extractant recovery column 200, and water 3 was separated to the lower portion. At this time, the operating temperature of the extraction column 100 was controlled to 40° C., and the operating pressure was controlled to 750 torr.

In the extractant recovery column 200, the extractant was separated as the upper discharge stream, and a part of the upper discharge stream from the extractant recovery column 200 was refluxed to the extraction column 100. The lower discharge stream from the extractant recovery column 200 including the acrylic acid was supplied to the first separation column 300. At this time, the operating temperature of the extractant recovery column 200 was controlled to 54.1° C. in the upper portion and 96.9° C. in the lower portion, and the operating pressure thereof was controlled to 110 torr.

In the first separation column 300, a low-boiling point by-product was separated to the upper portion, and the lower discharge stream including the acrylic acid was supplied to a second separation column 310. In addition, in the second separation column 310, a high-boiling point by-product was separated to the lower portion, and acrylic acid 4 was separated as the upper discharge stream.

At this time, the temperature, the pressure, and the flow rate (kg/hr) for each component in each stream are shown in the following Table 3:

TABLE 3

| | 1 | 2 | 3 | 4 |
|---|---|---|---|---|
| Temperature (° C.) | 40.0 | 40.0 | 40.0 | 96.9 |
| Pressure (torr) | 750 | 750 | 750 | 110 |
| Mass flow rate (kg/hr) | 923.2 | 3325.3 | 610.7 | 301.3 |
| Water | 600.0 | 13.6 | 588.3 | 0.0 |
| Toluene | 0.0 | 2999.0 | 0.5 | 0.0 |
| Acrylic acid | 303.1 | 310.9 | 3.3 | 299.9 |
| Hydroxyacetone | 20.0 | 1.4 | 18.6 | 1.4 |

TABLE 3-continued

| | | 1 | 2 | 3 | 4 |
|---|---|---|---|---|---|
| Mass fraction | Water | 0.650 | 0.004 | 0.963 | 0.000 |
| | Toluene | 0.000 | 0.902 | 0.001 | 0.000 |
| | Acrylic acid | 0.328 | 0.093 | 0.005 | 0.995 |
| | Hydroxy-acetone | 0.022 | 0.000 | 0.030 | 0.005 |
| | Total | 1 | 1 | 1 | 1 |

Comparative Example 2

The process was performed in the same manner as in Comparative Example 1, except that the flow rate of the extractant supplied to the extraction column 100 was controlled.

At this time, the temperature, the pressure, and the flow rate (kg/hr) for each component in each stream are shown in the following Table 4:

TABLE 4

| | | 1 | 2 | 3 | 4 |
|---|---|---|---|---|---|
| Temperature (° C.) | | 40.0 | 40.0 | 40.0 | 40.0 |
| Pressure (torr) | | 750 | 750 | 750 | 110 |
| Mass flow rate (kg/hr) | | 923.2 | 596.3 | 854.3 | 67.7 |
| Water | | 600.0 | 4.7 | 596.5 | 0.0 |
| Toluene | | 0.0 | 497.1 | 2.9 | 0.0 |
| Acrylic acid | | 303.1 | 94.0 | 235.4 | 67.2 |
| Hydroxyacetone | | 20.0 | 0.5 | 19.5 | 0.5 |
| Mass fraction | Water | 0.650 | 0.008 | 0.698 | 0.000 |
| | Toluene | 0.000 | 0.834 | 0.003 | 0.000 |
| | Acrylic acid | 0.328 | 0.158 | 0.276 | 0.993 |
| | Hydroxy-acetone | 0.022 | 0.001 | 0.023 | 0.007 |
| | Total | 1 | 1 | 1 | 1 |

Referring to Tables 1 to 4, in Examples 1 and 2 in which by-products were separated and an acrylic acid is recovered by the method for preparing an acrylic acid according to the present invention, it was confirmed that the purity of the acrylic acid was 99% or more, and the amount of the acrylic acid lost in the extraction column 100 was very small. In addition, it was confirmed that the total amount of hydroxyacetone included in the reaction product was discharged with water in the extraction column 100.

In comparison, in Comparative Example 1 in which the refining column 400 was not provided as compared with Example 1, it was confirmed that the amount of hydroxyacetone remaining in the upper discharge stream from the second separation column 310 was so large that the purity of the acrylic acid was low, and the amount of the acrylic acid lost in the extraction column 100 was increased.

In addition, in Comparative Example 2 in which the amount of the extractant supplied to the extraction column 100 was decreased for removing the total amount of hydroxyacetone from the extraction column 100 in Comparative Example 1, it was confirmed that the amount of the acrylic acid which was discharged with water in the extraction column 100 and lost was increased.

Comparative Example 3

According to the process flow diagram illustrated in FIG. 3, a process of preparing an acrylic acid was simulated, using an Aspen Plus simulator from Aspen Technology, Inc.

The process was performed in the same manner as in Example 1, except that the lower discharge stream 6 from the refining column 400 was discharged without being refluxed to the extraction column 100.

At this time, the temperature, the pressure, and the flow rate (kg/hr) for each component in each stream are shown in the following Table 5:

TABLE 5

| | | 1 | 2 | 3 | 4 | 5 | 6 |
|---|---|---|---|---|---|---|---|
| Temperature (° C.) | | 40.0 | 40.0 | 40.0 | 96.9 | 62.5 | 65.6 |
| Pressure (torr) | | 750 | 750 | 750 | 110 | 110 | 110 |
| Mass flow rate (kg/hr) | | 923.4 | 3325.3 | 612.0 | 305.5 | 300.0 | 5.6 |
| Water | | 600.0 | 13.7 | 588.3 | 0.0 | 0.0 | 0.0 |
| Toluene | | 0.0 | 2999.0 | 0.5 | 0.0 | 0.0 | 0.0 |
| Acrylic acid | | 303.4 | 308 | 4.4 | 299 | 294.8 | 4.2 |
| Hydroxyacetone | | 20.0 | 1.4 | 18.6 | 1.4 | 0.0 | 1.4 |
| Mass fraction | Water | 0.650 | 0.004 | 0.962 | 0.000 | 0.000 | 0.000 |
| | Toluene | 0.000 | 0.903 | 0.001 | 0.000 | 0.000 | 0.000 |
| | Acrylic acid | 0.329 | 0.093 | 0.007 | 0.995 | 1.000 | 0.750 |
| | Hydroxyacetone | 0.022 | 0.000 | 0.030 | 0.005 | 0.000 | 0.250 |
| | Total | 1 | 1 | 1 | 1 | 1 | 1 |

Comparative Example 4

The process was performed in the same manner as in Comparative Example 3, except that the flow rate of the extractant supplied to the extraction column 100 was controlled.

At this time, the temperature, the pressure, and the flow rate (kg/hr) for each component in each stream are shown in the following Table 6:

TABLE 6

| | | 1 | 2 | 3 | 4 | 5 | 6 |
|---|---|---|---|---|---|---|---|
| Temperature (° C.) | | 40.0 | 40.0 | 40.0 | 96.9 | 62.5 | 65.6 |
| Pressure (torr) | | 750 | 750 | 750 | 110 | 110 | 110 |
| Mass flow rate (kg/hr) | | 923.4 | 3325.3 | 612.0 | 305.5 | 300.0 | 5.6 |
| Water | | 600.0 | 14.1 | 589.9 | 0.0 | 0.0 | 0.0 |
| Toluene | | 0.0 | 5999.5 | 0.5 | 0.0 | 0.0 | 0.0 |
| Acrylic acid | | 303.4 | 318 | 4.6 | 298.7 | 294.8 | 3.9 |
| Hydroxyacetone | | 20.0 | 1.7 | 18.3 | 1.7 | 0.0 | 1.7 |
| Mass fraction | Water | 0.650 | 0.002 | 0.962 | 0.000 | 0.000 | 0.000 |
| | Toluene | 0.000 | 0.947 | 0.001 | 0.000 | 0.000 | 0.000 |
| | Acrylic acid | 0.329 | 0.050 | 0.008 | 0.994 | 1.000 | 0.696 |
| | Hydroxyacetone | 0.022 | 0.000 | 0.030 | 0.006 | 0.000 | 0.304 |
| | Total | 1 | 1 | 1 | 1 | 1 | 1 |

Referring to Tables 1, 2, 5, and 6, in Examples 1 and 2 in which by-products were separated and an acrylic acid is recovered by the method for preparing an acrylic acid according to the present invention, it was confirmed that the purity of the acrylic acid was 99% or more, and the amount of the acrylic acid lost in the extraction column 100 was very small. In addition, it was confirmed that the total amount of hydroxyacetone included in the reaction product was discharged with water in the extraction column 100.

In comparison, in Comparative Examples 3 and 4 in which the lower discharge stream from the refining column 400 was not refluxed to the extraction column 100 as compared with Example 1, it was confirmed that hydroxyacetone which was the by-product included in the stream introduced to the extraction column 100 was not all discharged as the lower discharge stream from the extraction column 100. When hydroxyacetone was discharged from the lower portion of the refining column 400, in order to prevent accumulation of hydroxyacetone which was not discharged as the lower discharge stream from the extraction column 100 in the system, it was confirmed that the acrylic acid was partially lost from the lower portion of the refining column 400.

In addition, in Comparative Example 4 in which the amount of the extractant supplied to the extraction column 100 was doubled for removing the total amount of hydroxyacetone from the extraction column 100 in Comparative Example 3, it was confirmed that in this case, the total amount of hydroxyacetone was not discharged from the extraction column 100 even with the increased amount of toluene as the extractant, and the amount of the acrylic acid which was discharged with water and lost was increased. In particular, the mass flow rate of the acrylic acid lost from the lower portion of the extraction column 100 in Comparative Example 4 to the mass flow rate of the acrylic acid lost from the lower portion of the extraction column 100 in Example 1 was increased by 35%.

Furthermore, in Comparative Examples 3 and 4 in which the lower discharge stream from the refining column 400 was not refluxed to the extraction column 100, it was confirmed that the acrylic acid having a high purity was able to be recovered from the upper portion of the refining column 400, but the yields of the high-purity acrylic acid was lower than those of Examples 1 and 2.

The invention claimed is:

1. A method for preparing an acrylic acid, the method comprising:

supplying a reaction product stream prepared by a dehydration reaction of a lactic acid aqueous solution to an extraction column, and in the extraction column, separating an upper discharge stream including an acrylic acid using an extractant and supplying the upper discharge stream to an extractant recovery column;

in the extractant recovery column, separating a lower discharge stream including the acrylic acid and supplying the lower discharge stream to a first separation column;

in the first separation column, separating a low-boiling point by-product to an upper portion, and separating a lower discharge stream including the acrylic acid and supplying the lower discharge stream to a second separation column;

in the second separation column, separating a high-boiling point by-product to a lower portion, and supplying an upper discharge stream including the acrylic acid to a refining column; and in the refining column, separating an upper discharge stream including the acrylic acid, and refluxing a lower discharge stream including hydroxyacetone to the extraction column, wherein water and hydroxyacetone are separated to a lower portion of the extraction column.

2. The method of claim 1, wherein the reaction product stream includes the acrylic acid, water, a low-boiling point by-product, a high-boiling point by-product, and hydroxyacetone.

3. The method of claim 1, wherein a ratio of a content of hydroxyacetone separated to the lower portion of the extraction column to a content of hydroxyacetone included in the reaction product stream is 0.95 to 1.

4. The method of claim 1, wherein a part of the upper discharge stream including the extractant in the extractant recovery column is refluxed to the extraction column.

5. The method of claim 1, wherein the extractant is one or more selected from the group consisting of benzene, toluene, xylene, n-heptane, cycloheptane, cycloheptene, 1-heptene, ethylbenzene, methylcyclohexane, n-butylacetate, isobutylacetate, isobutylacrylate, n-propylacetate, isopropylacetate, methylisobutylketone, 2-methyl-1-heptene, 6-methyl-1-heptene, 4-methyl-1-heptene, 2-ethyl-1-hexene, ethylcyclopentane, 2-methyl-1-hexene, 2,3-dimethylpentane, 5-methyl-1-hexene, and isopropylbutylether.

6. The method of claim 1, wherein the reaction product stream is a condensate condensed through a cooling tower.

7. The method of claim 1, wherein a content of hydroxyacetone in the upper discharge stream from the extraction column is 0.2% to 15% of a content of hydroxyacetone included in the reaction product stream.

8. The method of claim 1, wherein the upper discharge stream from the second separation column is supplied to one stage among stages corresponding to 50% to 90% of a total number of stages of the refining column.

9. The method of claim 1, wherein an operating temperature of the extractant recovery column is 40° C. to 150° C., and an operating pressure thereof is 35 torr to 300 torr.

10. The method of claim 1, wherein an operating temperature of the refining column is 60° C. to 200° C., and an operating pressure thereof is 35 torr to 500 torr.

* * * * *